United States Patent
Drasler et al.

(10) Patent No.: US 9,427,217 B2
(45) Date of Patent: Aug. 30, 2016

(54) APPARATUS AND METHOD FOR CLOSING AN OPENING IN A BLOOD VESSEL USING MEMORY METAL AND COLLAGEN

(75) Inventors: William J. Drasler, Minnetonka, MN (US); Tracee Eidenschink, Wayzata, MN (US); Joseph M. Thielen, Buffalo, MN (US); Mark L. Jenson, Greenfield, MN (US); Anu Sadasiva, Maple Grove, MN (US)

(73) Assignee: BOSTON SCIENTIFIC SCIMED INC., Maple Grove, MN (US)

( * ) Notice: Subject to any disclaimer, the term of this patent is extended or adjusted under 35 U.S.C. 154(b) by 2441 days.

(21) Appl. No.: 12/026,046

(22) Filed: Feb. 5, 2008

(65) Prior Publication Data
US 2008/0312683 A1    Dec. 18, 2008

Related U.S. Application Data

(60) Provisional application No. 60/888,211, filed on Feb. 5, 2007.

(51) Int. Cl.
*A61B 17/00* (2006.01)

(52) U.S. Cl.
CPC .. *A61B 17/0057* (2013.01); *A61B 2017/00004* (2013.01); *A61B 2017/00637* (2013.01); *A61B 2017/00654* (2013.01); *A61B 2017/00672* (2013.01); *A61B 2017/00867* (2013.01)

(58) Field of Classification Search
CPC ............... A61B 17/0057; A61B 2017/00637; A61B 2017/00672; A61B 2017/00867

USPC ............... 606/151, 157, 213, 232, 158, 215
See application file for complete search history.

(56) References Cited

U.S. PATENT DOCUMENTS

| | | | | |
|---|---|---|---|---|
| 4,878,906 A * | 11/1989 | Lindemann et al. | ........ | 623/3.18 |
| 5,312,435 A | 5/1994 | Nash et al. | | |
| 5,405,378 A * | 4/1995 | Strecker | ........ | 623/1.12 |
| 5,531,759 A * | 7/1996 | Kensey et al. | ........ | 606/213 |
| 5,700,277 A | 12/1997 | Nash et al. | | |
| 5,941,900 A * | 8/1999 | Bonutti | ........ | 606/232 |
| 5,980,559 A * | 11/1999 | Bonutti | ........ | 606/232 |
| 6,045,570 A | 4/2000 | Epstein et al. | | |
| 6,110,184 A | 8/2000 | Weadock | | |
| 6,183,496 B1 * | 2/2001 | Urbanski | ........ | 606/213 |
| 6,837,893 B2 * | 1/2005 | Miller | ........ | 606/139 |
| 7,556,632 B2 * | 7/2009 | Zadno | ........ | 606/142 |

(Continued)

FOREIGN PATENT DOCUMENTS

WO    2007/025017 A2    3/2007
WO    2008/097967 A2    8/2008

*Primary Examiner* — Alexander Orkin
(74) *Attorney, Agent, or Firm* — Seager, Tufte & Wickhem LLP

(57) ABSTRACT

An apparatus and method for closing an arteriotomy site are disclosed which may employ the use of a delivery sheath within which is provided an anchoring device formed of memory metal wherein the anchoring device can be extended into the blood vessel itself. The memory metal, has a linear insertion configuration and obtains a non-linear or coiled configuration which can then be pulled back against the inner surface of the blood vessel to form a backstop. A biodegradable plug is then introduced into the tissue tract until it engages the backstop thereby ensuring proper positioning of the biodegradable plug. The anchoring device can then be retracted through the biodegradable plug leaving the arteriotomy site substantially closed with hemostasis being formed therearound.

2 Claims, 7 Drawing Sheets

(56) References Cited

U.S. PATENT DOCUMENTS

| | | | |
|---|---|---|---|
| 8,088,144 B2* | 1/2012 | Ginn et al. | 606/213 |
| 2002/0072768 A1* | 6/2002 | Ginn | 606/213 |
| 2005/0010248 A1* | 1/2005 | Lafontaine | 606/213 |
| 2005/0085856 A1* | 4/2005 | Ginn | 606/213 |
| 2005/0228443 A1* | 10/2005 | Yassinzadeh | 606/213 |
| 2006/0034930 A1* | 2/2006 | Khosravi et al. | 424/484 |
| 2007/0083231 A1* | 4/2007 | Lee | 606/213 |
| 2007/0203506 A1 | 8/2007 | Sibbitt, Jr. et al. | |

* cited by examiner

FIG. 12a
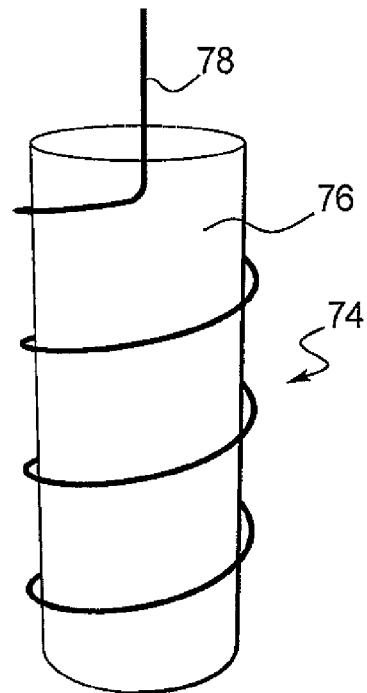
FIG. 12b
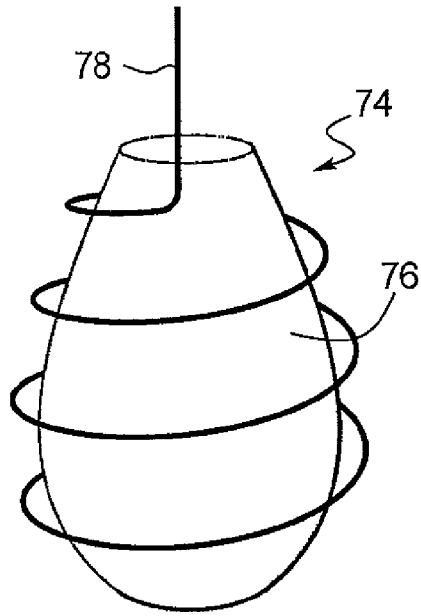
FIG. 13
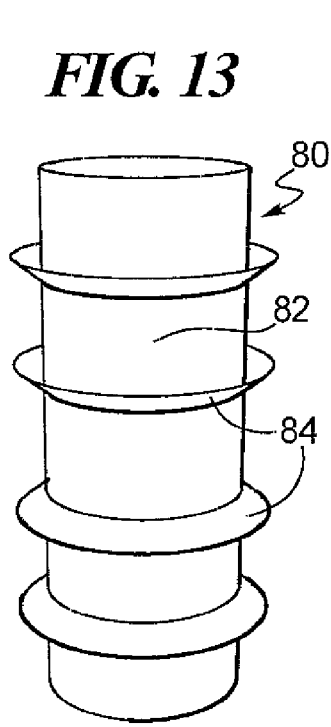
FIG. 14a
FIG. 14b
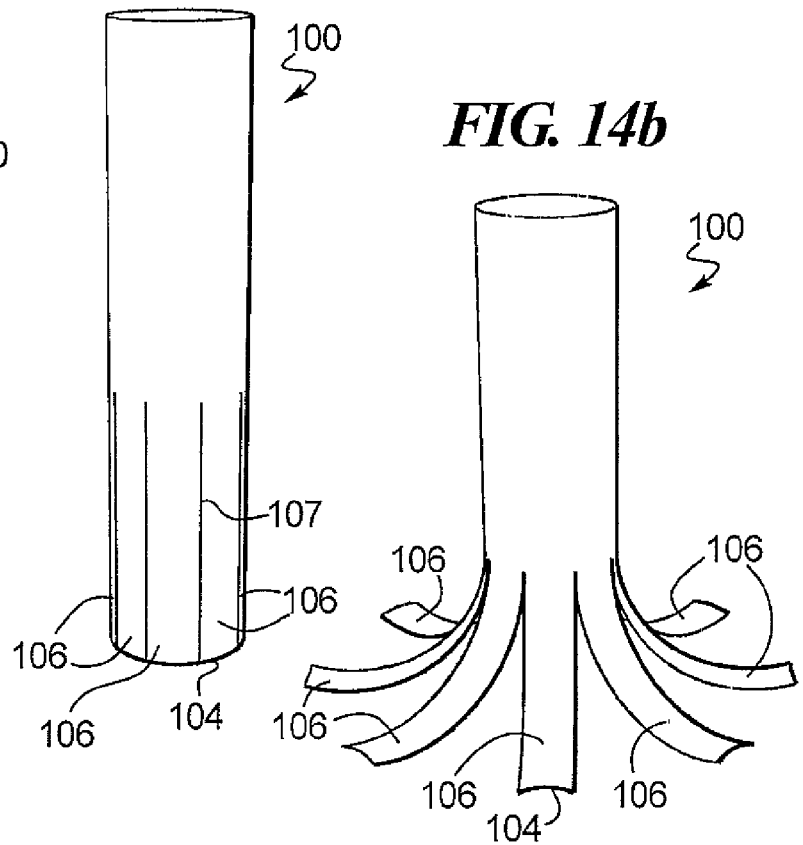

APPARATUS AND METHOD FOR CLOSING AN OPENING IN A BLOOD VESSEL USING MEMORY METAL AND COLLAGEN

CROSS-REFERENCE TO RELATED APPLICATION

This application is a non-provisional patent application claiming priority under 35 USC §119(e) to U.S. provisional patent application Ser. No. 60/888,211 filed on Feb. 5, 2007.

FIELD OF THE DISCLOSURE

The present disclosure generally relates to medical devices and, more particularly, relates to medical devices for closing an arteriotomy.

BACKGROUND OF THE DISCLOSURE

In many medical procedures, such as balloon angioplasty and the like, it is known how to create an opening in a blood vessel, known as an arteriotomy, to allow for the insertion of various medical devices which can be navigated through the blood vessel to the site to be treated Typically, the opening is formed in the femoral artery at a point proximate the groin and a series of medical devices are inserted in sequence. For example, a guide wire may first be inserted through the tissue tract created between the skin or the epidermis of the patient down through the subcutaneous tissue and into the opening formed in the blood vessel. The guide wire is then navigated through the blood vessel to the site of the occlusion, the heart, or any other area to be treated. Once the guide wire is in place, an introducer sheath can be slid over the guide wire to form a wider, more easily accessible, tract between the epidermis and the opening into the blood vessel. If an angioplasty needs to be performed, the balloon catheter can then be introduced over the guide wire again through the introducer sheath, through the opening in the femoral artery, and then up the blood vessel to the site of the occlusion.

Once the procedure is performed, the guide wire, balloon catheter and any other equipment introduced can be retracted through the blood vessel, out through the opening in the blood vessel wall, out through the introducer sheath, and out of the body entirely The introduced sheath can then be removed and the physician or other medical technician is presented with the challenge of trying to close the opening both in the femoral artery and the tissue tract formed in the epidermis and subcutaneous tissue Most importantly, the opening in the blood vessel must be closed as soon as possible.

Over the years that these procedures have been performed, a number of apparatus and methods have been created for closing the opening in the blood vessel. Traditionally, and still commonly today, the opening is closed simply by the application of manual pressure If sufficient pressure is applied, the blood vessel is constricted until a clot or thrombus forms whereupon the pressure can be removed and eventually the patient can become ambulatory once again However, a number of drawbacks are associated with such a method. For one, the process is very time consuming often taking many hours for the thrombus to fully form, during which time the patient is required to be stationary. In addition, the mere application of such significant pressure to the groin is often quite uncomfortable for the patient.

In light of these difficulties, a number of proposals have been introduced to potentially alleviate such drawbacks. In one approach, an anchor is inserted through the tissue tract and the blood vessel with a filament extending therefrom and connected to a sealing plug by a pulley arrangement. Once the anchor engages an interior surface of the blood vessel the filament can be used to pull the sealing plug securely into the tissue tract. While this approach does more quickly close the opening in the blood vessel than manual pressure application, it also results in the unfavorable characteristic of leaving a foreign body in the patient after the procedure is completed.

Another approach uses a resistive heating coil inserted into the opening in the blood vessel. Upon energization of the heating coil, the blood in the vicinity of the opening is caused to coagulate given the rise in temperature. This can be accomplished in combination with the introduction of a procoagulant into the site to again expedite the creation of the coagulation. While this approach has also met with some level of success, it also results in the introduction of a foreign body and/or substance into the tissue of the patient.

A still further approach involves the introduction of a collagen plug into the site of the opening. Such a plug is sized to be frictionally engaged by the sides of the opening in the blood vessel and thus held in place until coagulation of blood forms around the collagen plug. The collagen plug is biodegradable and eventually is dispersed into the blood flow and eliminated from the body. However, just the introduction of such a foreign substance into the body can sometimes be, at the very least, inflammatory and uncomfortable for the patient.

In one collagen plug approach, a balloon catheter is inserted into the blood vessel, inflated, and then pulled back against an interior surface of the blood vessel wall to serve as a backstop. The collagen plug in such an approach is shaped and sized as to closely match the opening in the blood vessel wall and is pushed down into the tissue tract until it engages the inflated balloon. The inflated balloon can then be deflated and withdrawn leaving the collagen plug in place.

In another collagen plug approach, a delivery sheath wider than the opening in the blood vessel wall is used and then a collagen plug corresponding to the size of the inner diameter of the delivery sheath is pushed through the sheath so as to engage the outer surface of the blood vessel wall The plug can then be tamped or compressed down against the exterior surface of the blood vessel wall such that a portion of the collagen extends into the opening of the blood vessel wall.

While each of the foregoing approaches have been met with some level of success, it can be seen that each also has substantial drawbacks Accordingly, it would be advantageous for the art to provide an apparatus and method which can quickly close the opening in the blood vessel wall, forms a thrombus which reliably remains in place after formation, minimizes patient discomfort, introduces no foreign body or substance into the blood vessel and leaves no foreign bodies behind after the procedure is completed.

SUMMARY OF THE DISCLOSURE

In accordance with one aspect of the disclosure, an apparatus for closing an opening in a blood vessel is disclosed which comprises an anchoring device having a linear insertion configuration and a non-linear deployed configuration, as well as a collagen plug adapted to be inserted through a tissue tract against the anchoring device when the anchoring device is in the deployed configuration.

In accordance with another aspect of the disclosure, a method of closing an opening in a blood vessel is disclosed which comprises inserting a delivery sheath into a tissue tract running from an epidermal layer of a patient to an arteriotomy site in a blood vessel, extending an anchoring device from the delivery sheath and into the blood vessel, the anchoring device being formed of a shape-memory alloy, the anchoring device being held in a linear configuration when within the delivery sheath and, assuming a non-linear configuration when extended from the delivery sheath, retracting the delivery sheath and anchoring device a distance sufficient to engage the anchoring device with an inner surface of the blood vessel proximate the arteriotomy site, pushing a collagen plug down the tissue tract until the plug engages the anchoring device, and pulling the anchoring device from the blood vessel, through the collagen plug and out of the tissue tract.

In accordance with another aspect of the disclosure, an apparatus for closing an opening in a blood vessel is disclosed comprising a delivery sheath having a distal end and a proximal end, the delivery sheath being insertable into a tissue tract running from an epidermal layer to an arteriotomy site, and a length of memory-metal positioned within the delivery sheath, the memory metal being substantially linear in shape when within the delivery sheath, and being substantially non-linear in shape when extended from the delivery sheath.

In accordance with another aspect of the disclosure, an apparatus for closing an opening in a blood vessel is disclosed comprising a collagen plug and a thread wrapped around the collagen plug, the collagen plug being compressed when the thread is taut.

In accordance with yet another aspect of the disclosure, an apparatus for closing an opening in a blood vessel is disclosed comprising a collagen plug having a relatively dense, hard upper portion, and a relatively malleable, soft lower portion.

These and other aspects and features of the disclosure will become more apparent upon reading the following detailed description when taken in conjunction with the accompanying drawings

BRIEF DESCRIPTION OF THE DRAWINGS

FIG. 12a is a perspective view of another alternative embodiment of a collagen plug with a thread spiral wound thereabout and in a compressed state;
FIG. 12b is a perspective view of the biodegradable plug of FIG. 12a, but with the thread being loosened and the collagen plug thereby being expanded;
FIG. 13 is a perspective view of yet another embodiment of a biodegradable plug including retention barbs;
FIG. 14a is a perspective view of another embodiment showing a plug with slits in an insertion configuration;
FIG. 14b is a perspective view of the embodiment of FIG. 14a in a flared, deployed configuration.

Figure 1:
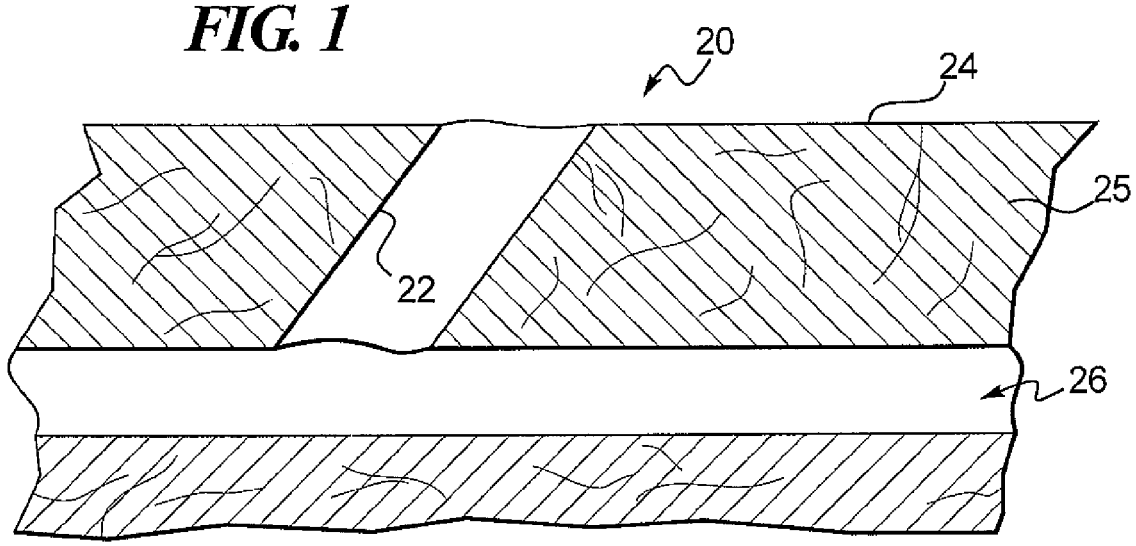
FIG. 1 is a sectional view depicting an arteriotomy site with a tissue tract being formed from an epidermal layer to an opening in a blood vessel to be closed.

While the present disclosure is susceptible to various modifications and alternative constructions, certain illustrative embodiments thereof have been shown in the drawings and will be described below in detail. It should be understood, however, that there is no intention to limit the invention to these specific forms disclosed, but on the contrary, the intention is to cover all modifications, alternative constructions, and equivalents falling within the spirit and scope of the present invention.

DETAILED DESCRIPTION OF THE DISCLOSURE

Referring now to the drawings and with specific reference to FIG. 1, an arteriotomy site 20 is depicted in cross-section. As shown therein, a tissue tract 22 is formed extending between an epidermal layer 24 through a subcutaneous layer 25 and a blood vessel 26. As will be readily understood by one of ordinary skill in the art, the arteriotomy site 20 can be formed for any number of different medical procedures including, but not limited to, balloon angioplasty, wherein the arteriotomy is typically formed in a femoral artery to allow for the passage of guide wires, balloon catheters, and other medical devices therethrough. A balloon catheter can be navigated to the site of the occlusion and expanded to clear the occlusion. In addition, other medical devices can then be inserted and navigated to the site so as to deploy a stent or other similar type of medical device. After the medical procedure is completed, all such medical devices need to be removed from the blood vessel and through the tissue tract whereupon the site of the arteriotomy must be closed to prevent bleeding.

Figure 2:
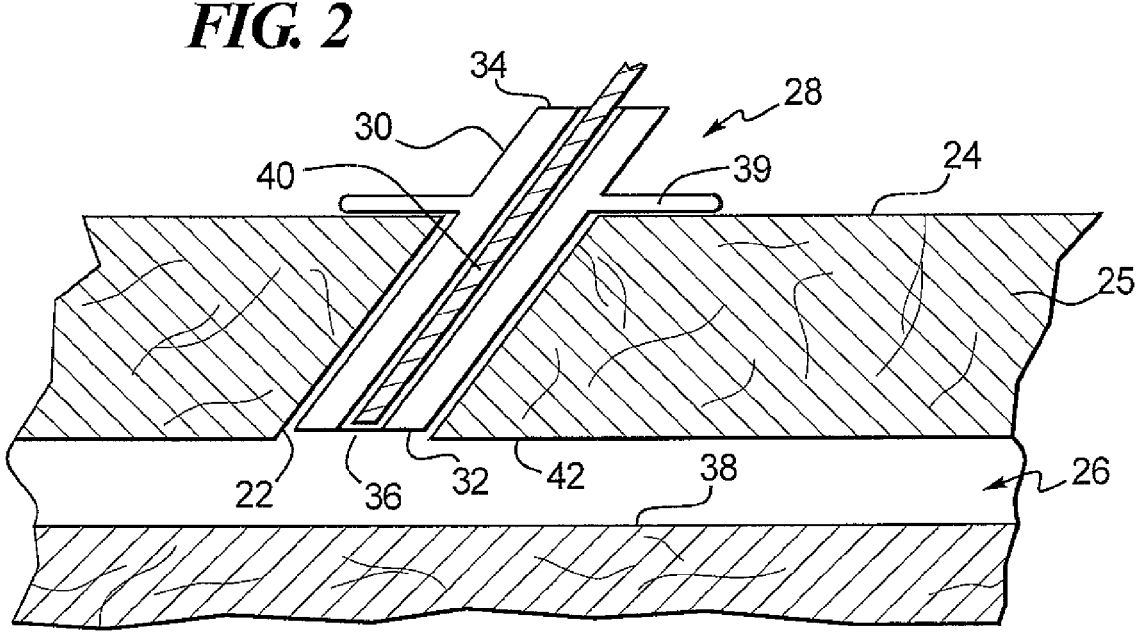
FIG. 2 is a sectional view similar to FIG. 1, but with a delivery sheath and anchoring device being initially inserted.
Figure 3:
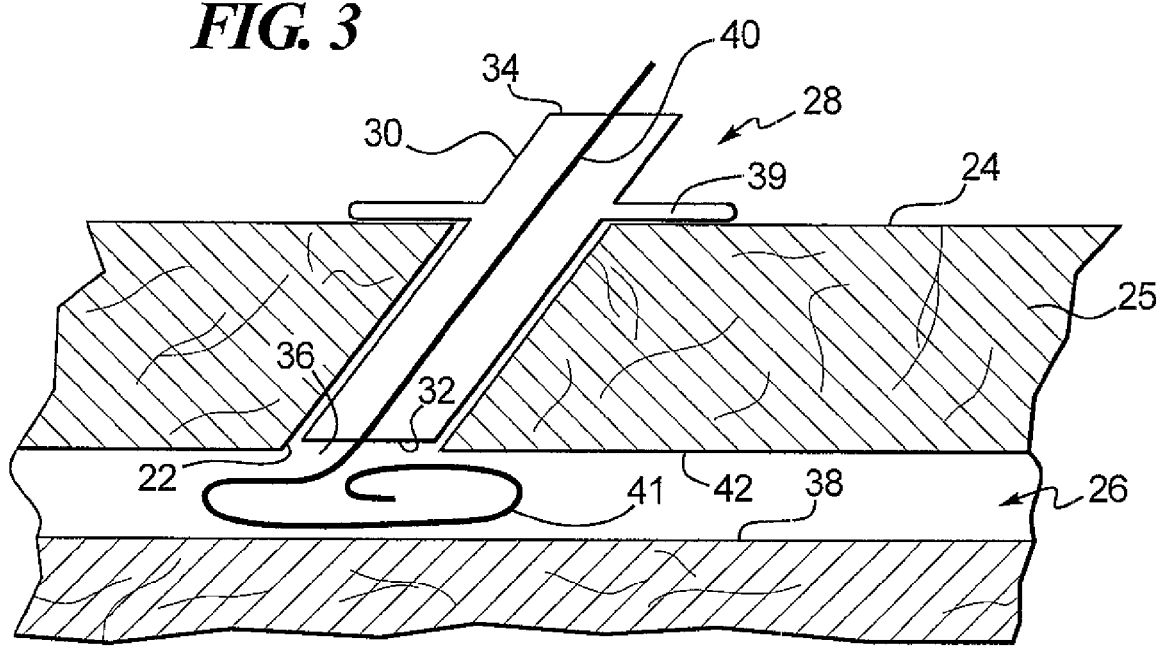
FIG. 3 is a sectional view similar to FIG. 2, but with the anchoring device being deployed from the delivery sheath.

Turning now to FIG. 2, the apparatus for closing the arteriotomy site is depicted as system 28. As shown therein, the system 28 may include a delivery sheath 30 which could be of a substantially tubular configuration having a distal end 32 and a proximal end 34 The delivery sheath 30 is introduced into the tissue tract 22 until the distal end 32 is proximate an opening 36 formed in a blood vessel wall 38 of the blood vessel 26. An optional circumferential flange 39 or other indicia may be provided on the delivery sheath to inform the physician or other medical technician that the delivery sheath is inserted to the correct depth Within the delivery sheath 30 is an anchoring device 40. The anchoring device 40 may be of a linear configuration when held within the delivery sheath 30, but be of a non-linear configuration when extended from the delivery sheath as shown in FIG. 3. Any number of different materials can be used to form the anchoring device 40 with shape memory metal alloys being one subset of suitable materials Such shape memory metals include, but are not limited to, nickel-titanium alloys (commonly marketed under the Nitinol™ trademark), cobalt-chromium-nickel alloys (commonly marketed under the Elgiloy™ trademark). Such shape memory alloys are often referred to by the acronym SMAs and exhibit two main properties, namely, that they are pseudo-elastic, and have the shape memory effect. These features are particularly helpful to the present disclosure in that the anchoring device 40 has sufficient elasticity to be held in a linear configuration depicted in FIG. 2, but when freed from the delivery sheath 30, reverts to its non-linear or coiled configuration thus serving as an anchor for the system 28.

Figure 4:
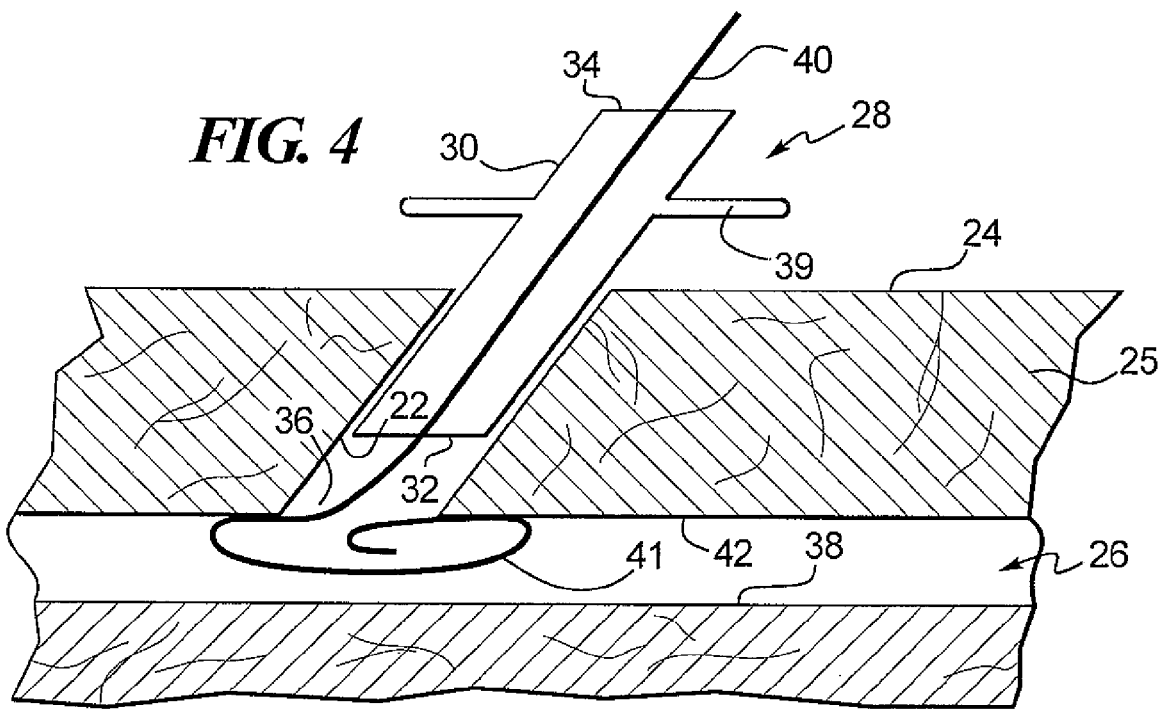
FIG. 4 is a sectional view similar to FIG. 3, but with the anchoring device being deployed and retracted against the inner surface of the blood vessel wall.
Figure 5:
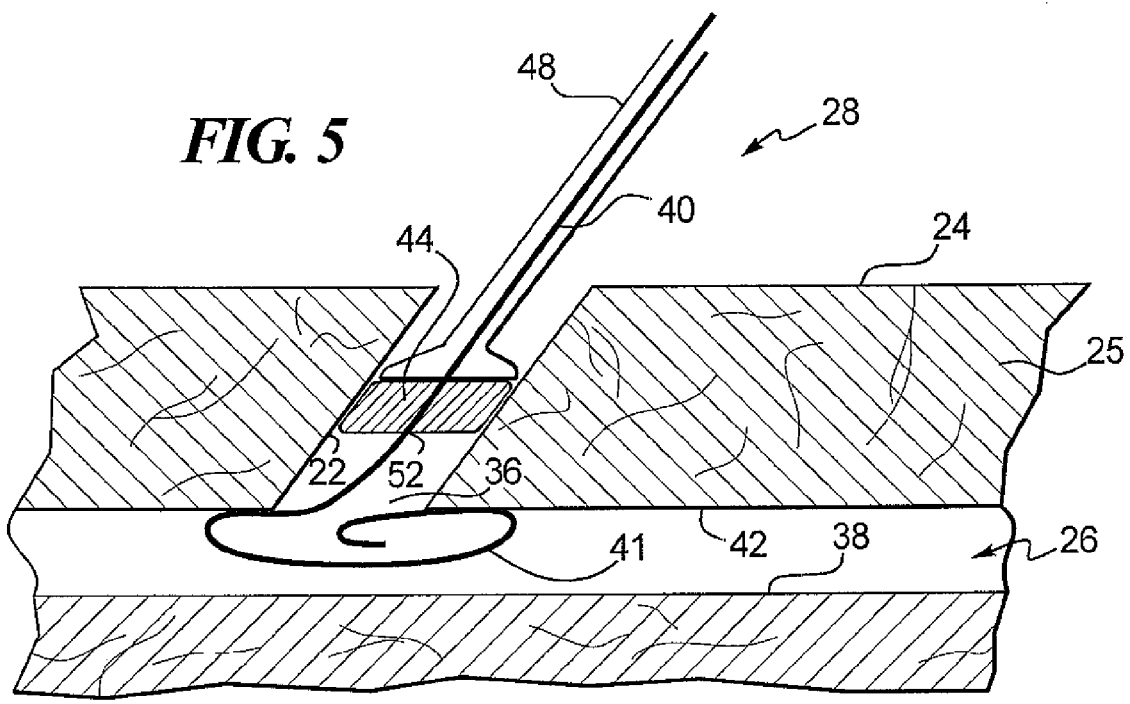
FIG. 5 is a sectional view similar to FIG. 4, but with the anchoring device being deployed and a biodegradable plug being inserted.
Figure 6:
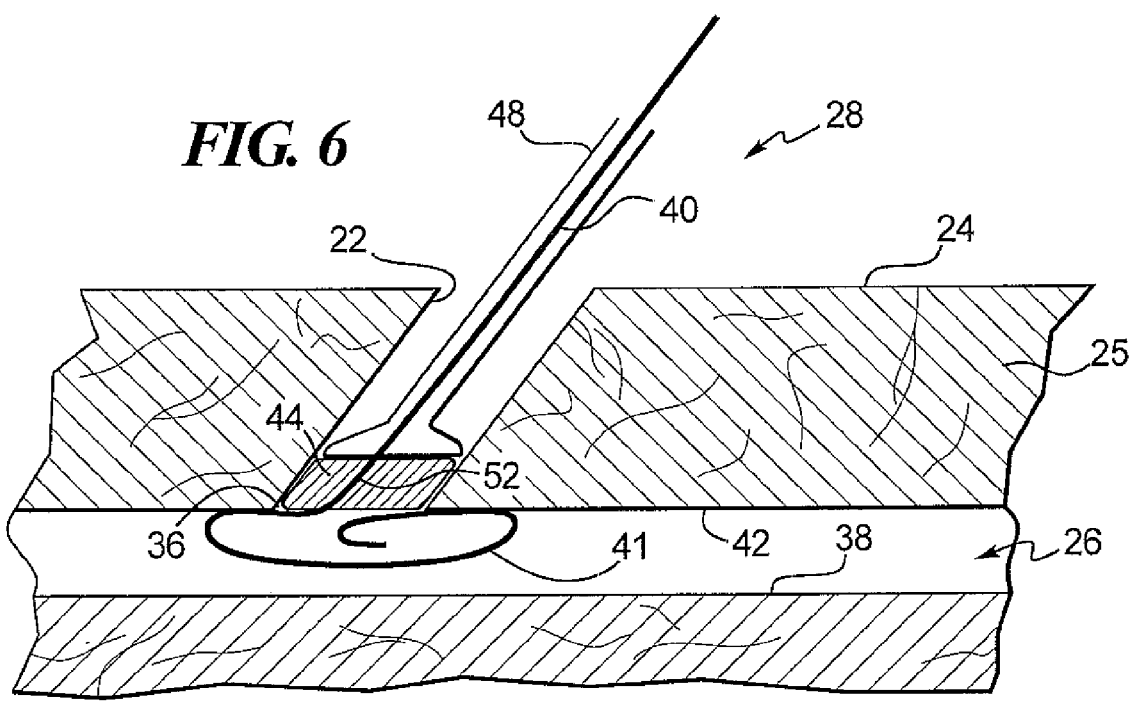
FIG. 6 is a sectional view similar to FIG. 5, but with the biodegradable plug being tamped down against the anchoring device by a ram rod.

Referring again to the drawings and with specific reference to FIGS. 3 and 4, it can be seen that once the anchoring device 40 is extended from the delivery sheath 30, it forms the non-linear backstop 41 or configuration of FIG. 3. As will be described in further detail herein, that non-linear configuration can result in any number of different shapes with coiled or clover-leaf shapes being two examples. In addition, as can be seen from FIG. 3, the deployed configuration is formed within the blood vessel 26 itself. Accordingly, when the delivery sheath 30 and anchoring device 40 are both retracted within the tissue tract 22, the anchoring device 40 engages an inner surface 42 of the blood vessel wall 38. While such an anchoring device 40 does not seal the tissue tract 22, it does form a sufficient backstop 41 fbi the introduction of a collagen plug 44 as shown in FIG. 5 As shown, the collagen plug 44 is of a size sufficient to substantially extend across the width 46 of the tissue tract 22 and in the depicted embodiment is substantially cylindrical in shape. The collagen plug 44 can be introduced into the tissue tract 22 itself, through the delivery sheath 30, through an introducer sheath (not shown), or any other suitable mechanism. In order to ensure proper placement of the collagen plug 44, it can be seen from FIG. 6, that a ram or tamping rod 48 may be used to compress the collagen 44 down into the tissue tract 22 against the anchoring device 40. By pulling the anchoring device 40 up against the inner surface 42 of the blood vessel wall 38, the backstop surface 41 is formed against which the collagen plug 44 can be pushed.

Figure 7:
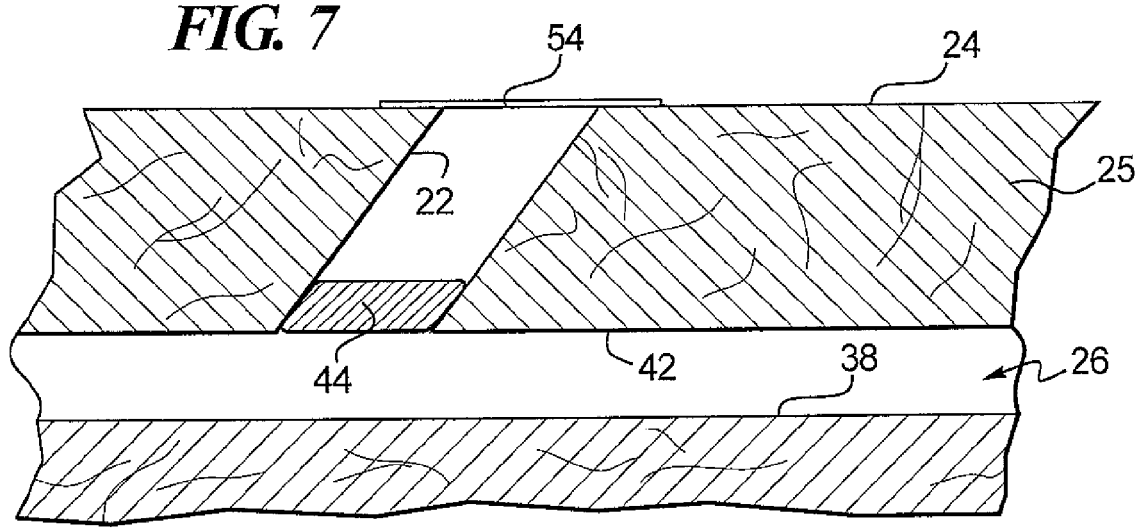
FIG. 7 is a sectional view similar to FIG. 6, but after the anchoring device has been removed, the biodegradable plug has been fully inserted, and a bandage layer has been placed over the epidermal layer.

Referring now to FIG. 7, when the collagen plug 44 is fully deployed and inserted into the tissue tract 22 so as to substantially seal blood flow from the blood vessel 26 into the tissue tract 22, the anchoring device 40 can be retracted through a aperture 52 (see FIG. 6) formed within the collagen plug 44 In so doing, the collagen plug 44 remains within the tissue tract 22, and a suitable bandaging material 54 can then be applied across the epidermis 24 allowing for the tissue tract 22 to fully close over time. It can therefore be seen that the apparatus and method disclosed herein provide for a way of closing an arteriotomy site 20 which, even during application, results in relatively limited occlusion of blood flow through the blood vessel 26 leaving only a biodegradable plug in the tissue tract 22. It is important to also note that the plug 44 need not be made of collagen, but any other material suitable for sealing such as, but not limited to, fibrin, PLA (polyactic acid), PLGA (poly(lactic-co-glycolic) acid), and PEG (polyethylene glycol).

Figure 8:
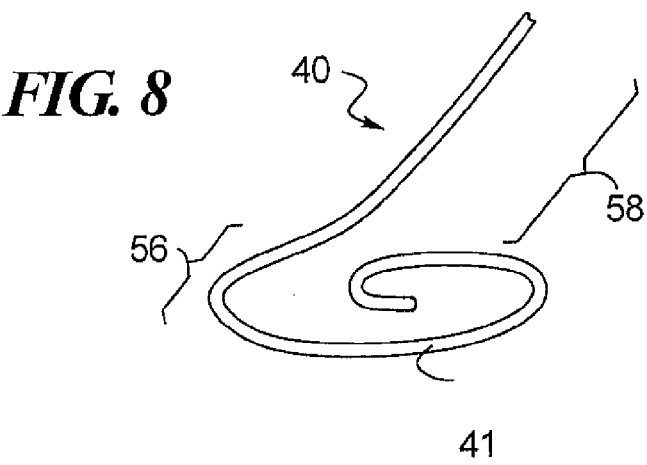
FIG. 8 is a perspective view of an anchoring device in a deployed configuration.
Figure 9:
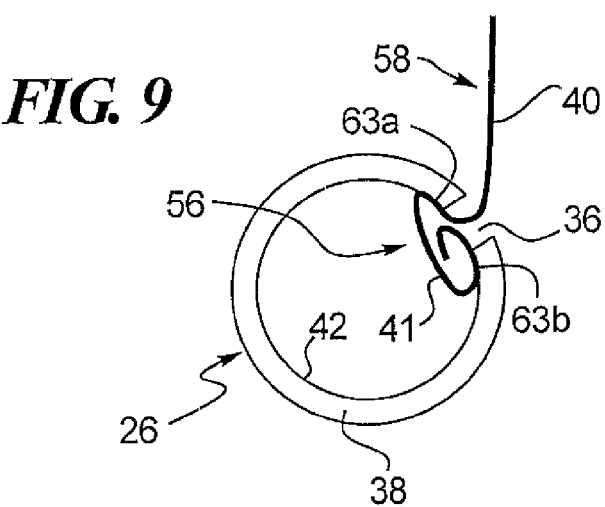
FIG. 9 is a sectional view of a blood vessel with an anchoring device being inserted therein and depicting the pivotable nature of the anchoring device.
Figure 10A:
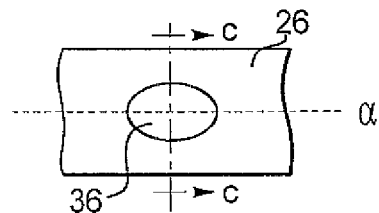
FIG. 10a is a top view of a blood vessel with a top stick.
Figure 10B:
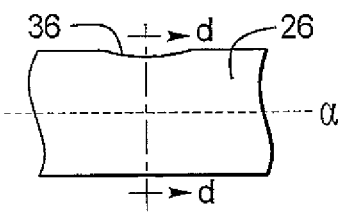
FIG. 10b is a top view of a blood vessel with a side stick.
Figure 10C:
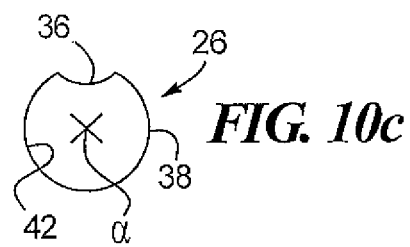
FIG. 10c is a lateral cross-section of the blood vessel of FIG. 10a taken along line c-c.
Figure 10D:
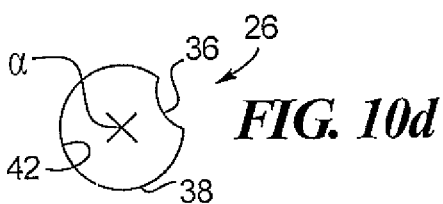
FIG. 10d is a lateral cross-section of the blood vessel of FIG. 10b taken along line d-d.
Figure 11A:
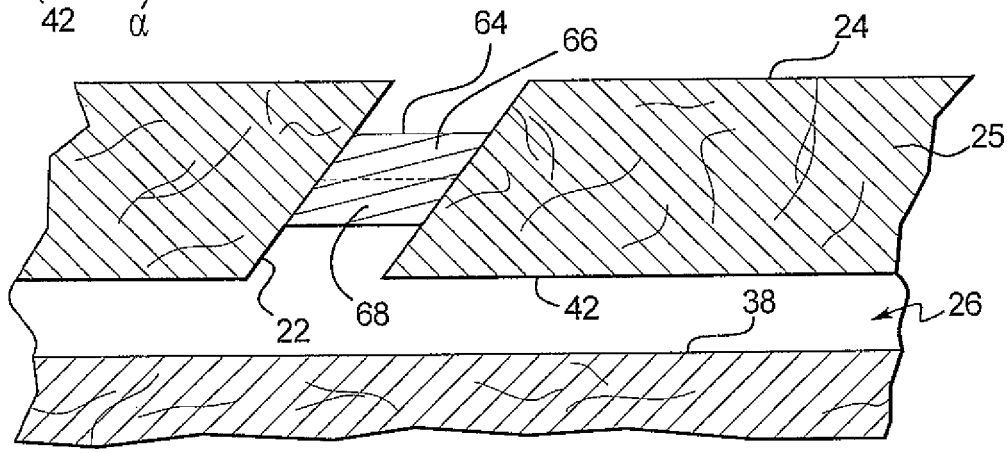
FIG. 11a is a sectional view of an alternative embodiment of a collagen plug being inserted.
Figure 11B:
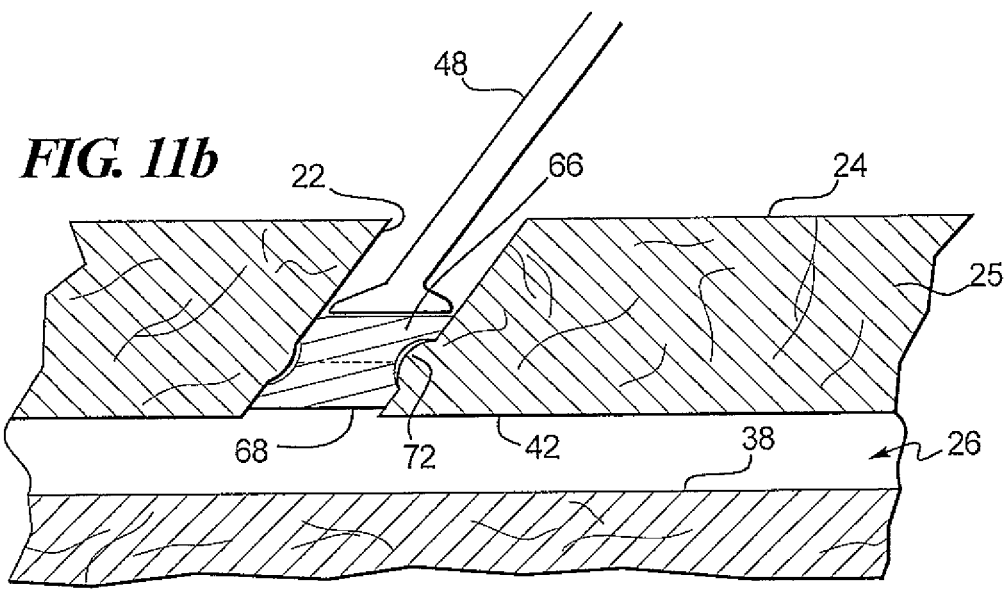
FIG. 11b is a sectional view of the alternative embodiment of FIG. 11a, but with the collagen plug being fully deployed.

Referring now to FIGS. 8 and 9, the anchoring device 40 is shown in a deployed configuration both in perspective of FIG. 8, and in cross-sectional view shown in FIG. 9. It will be readily understood that the anchoring device 40 is naturally in a non-linear configuration depicted by area 56 of FIG 8. If the entire anchoring device 40 is made of memory metal, the linear configuration of area 58 of FIG. 8 is only held in such a state by a delivery sheath 30 or the like as shown in FIG. 2. Alternatively, the linear area 58 may be made of traditional metal or other static material, with only the non-linear area 56 being made of memory metal. However, in the depicted embodiment the entire length of the anchoring device 40 is formed of a memory metal having the elasticity and shape memory effect referenced above. This is of importance for many reasons, one of which is depicted in FIG. 9.

As shown therein, with the blood vessel 26 depicted in a lateral cross-section, if the opening 36 is formed in a side of the blood vessel (known in the medical arts as a "side-stick"), the anchoring device 40 is sufficiently elastic so as to allow for the pivoting of a linear area 58 relative to a non-linear area 56. As an aside, it is important for the reader to understand the difference between a "side-stick" and a "top-stick". Referring to FIGS. 10a-d, that difference is explained. As shown therein, the blood vessel 26 includes a longitudinal axis denoted by the Greek letter α. If the physician is accurate when making the incision in the blood vessel 26, the opening 36 will be formed such that the longitudinal axis α extends substantially through the center of the opening 36. This is known as a "top-stick" and is shown in top view in FIG. 10a and in lateral cross-section in FIG. 10c If, however, as is often the case, the incision is made to the left or right of the longitudinal axis α anywhere from immediately next to the longitudinal axis α to tangential to the blood vessel 26, the opening 36 is known as a "side-stick". This is of importance for anchoring and closing purposes in that as best shown in the sectional views of FIGS. 10c and 10d, with a "top-stick" the opening is relatively uniform and symmetrical, but with a "side-stick", the opening extends down and away relative to the skin of the patient. Accordingly, to best close such an opening, the anchor must move to be aligned with both sides of the opening, and the collagen plug or other form of closure must be shaped or compressed to fill that resulting shape of the opening 36. This challenge is made even more difficult when it is considered that the tissue tract 22 meets the blood vessel 26 at an acute angle (typically 45°) thus often resulting in a compound angle, and the closure procedure is performed without the physician or other medical technician being able to physically see the opening 36.

The present disclosure aids in these respects however More specifically, when the physician or other medical technician deploys the anchoring device 40 and retracts the backstop 41 against the inner surface 42 of the blood vessel wall 38, the anchoring device 40 is able to pivot to a degree sufficient to allow for adequate contact of the backstop 41 against both sides 63a and 63b of the blood vessel wall 38 proximate to the opening 36 as shown in FIG. 9. A suitable backstop 41 is thereby formed allowing for proper insertion of the collagen plug 44. While not depicted, it can be readily understood that the teachings of the disclosure are equally applicable to side-sticks which would be provided on the opposite side or left side of FIG. 9, as well as the aforementioned top-sticks, wherein the insertion would be formed in the top of the blood vessel with respect to FIG. 9.

Another feature of the pending disclosure is the ability of the collagen plug 44 to remain within the tissue tract 22. Three embodiments of a collagen plug having such enhanced features are depicted in FIGS. 11a through 13. Starting with FIGS. 11a and b, one example of such a collagen plug is depicted as a plug 64. As shown first in an intermediate insertion stage of FIG. 11a, the plug 64 may be formed entirely of collagen, but may include an upper portion 66 and a lower portion 68. The upper portion 66 may have a relatively high density so as to be relatively hard, while the lower portion 68 may have a relatively low density so as to be relatively malleable or soft The plug 64 may be a composite of collagen and a hardening agent. The difference in hardness levels is of importance in that, as can be seen in a comparison between FIGS. 11a and 11b, as the plug 64 is inserted through the tissue tract 22, the relatively hard upper portion 66 serves to grasp inner surfaces 70 of the tissue tract 22. In so doing, tissue 72 is gathered between the upper portion 66 and lower portion 68 thereby increasing the surface area of tissue being held and increasing the frictional interference between the plug 64 and tissue tract 22. In addition, by providing the lower portion 68 of relatively soft or malleable collagen, it can better conform to the shape of the opening 36 formed in the blood vessel wall 38 For example, if the opening 36 is a side-stick as depicted in FIGS. 9 and 10, such a soft, malleable portion 68 can, upon application of adequate insertion force, alter its shape to best fill the shape of the side-stick opening.

Referring now to FIGS. 12a and 12b, another alternative embodiment of the collagen plug is depicted by element 74. As shown therein, the plug 74 includes a substantially cylindrical body 76 of collagen with a vicryl thread or filament 78 spirally wound thereabout. When the filament or thread 78 is pulled taut, the plug 74 maintains the cylindrical shape depicted in FIG. 12a, and when the thread is relatively loose about the plug 74, the plug 74 obtains the relatively bulbous shape depicted in FIG. 12b The applicability of this plug to such an arteriotomy closure application can be readily understood More specifically, the tight configuration depicted in FIG. 12a could be used when the plug 74 is being inserted through the tissue tract 22 and then once it reaches its deployment location, i.e., proximate the blood vessel wall itself, the string or filament can be loosened thereby allowing the plug to expand and increase the frictional engagement between the plug 74 and the tissue tract 22.

With respect to FIG. 13, a still further embodiment of a plug is depicted by element 80. As opposed to the collagen plugs previously depicted, an exterior surface 82 of the plug 80 can be formed with a series of barbs 84 or other protrusions. In the depicted embodiment, it can be seen that the barbs 84 are formed with angled surfaces 86 with some of the angled surfaces 86 extending upwardly and some the angled surfaces 86 extending downwardly. In so doing, the barbs 84 prevent movement in both directions along the longitudinal axis of the plug 80. More specifically, the barbs 84 engage the tissue of the tissue tract 22 thereby increasing the frictional interference between the two and substantially preventing movement.

With respect to FIGS. 14a and 14b, a plug 100 is depicted having a plurality of slits 102 or other incisions therein. As shown, in an insertion configuration (FIG. 14a) the plug 100 is substantially cylindrical. However, in the deployed configuration (FIG. 14b), the plug 100 is flared on buckled at distal end 104. This configuration may be reached by applying compressive force in the distal direction, thereby causing the individual legs 106 to buckle and the slits 102 allowing such motion. In so doing, the distal end 104 has a much larger diameter to facilitate retention in the tissue tract or blood vessel wall.

Figure 15:
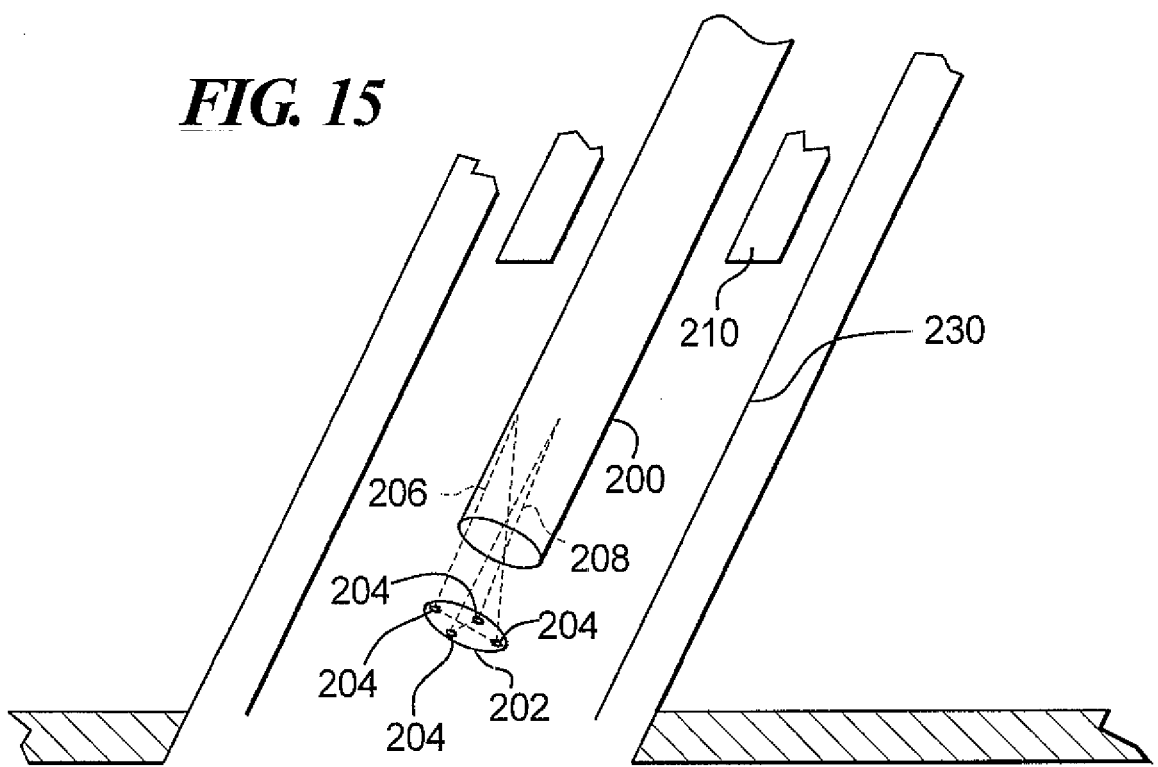
FIG. 15 is a sectional view of an embodiment having a separate retraction sheath.
Figure 16:
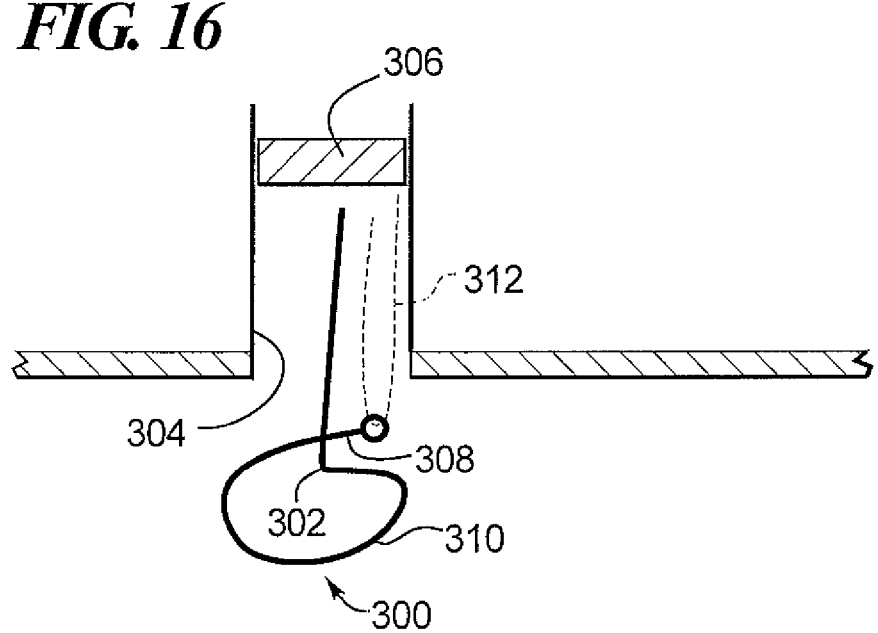
FIG. 16 is a sectional view of an embodiment having memory metal wire anchoring device with a sharp corner therein.

Referring now to FIG. 15, another embodiment is depicted which employs an anchoring device having a circular deployment configuration and a retraction sheath 200 separate from the delivery sheath 230. As shown therein the retraction sheath 200 houses a circular memory wire 202 with four retention loops 204. A first thread or filament 206 is strung through a pair of opposed loops 204, while a second thread or filament 208 is strung though a second pair of opposed loops 204. If each set of opposed loops 204 is held together, the circular wire 202 will not deform and a plug 210 can be pushed against it and serve as an anchor. In such an embodiment, the plug 210 can be annular in shape and be slid through the delivery sheath, but over the retraction sheath 200. After the plug is deployed, the threads 206 and 208 can be pulled to compress the wire 202, and the wire 202 can then be retracted out of the blood vessel through the retraction sheath 200. The plug 210 may have a thread wound through it to compress the plug while being pushed down the blood vessel, but allow the plug to expand when positioned appropriately In another embodiment, depicted in FIG. 16, a memory wire 300 with a sharp corner 302 (perhaps, a 90° turn) is used. As shown, when inserted, the wire 300 can be positioned such that the corner 302 is positioned directly below the tissue tract 304, thereby forming an anchoring device or shoulder against which a biodegradable plug 306 can be pushed. A distal end 308 of the wire 310 can have a retraction thread or filament 312 attached thereto. After the plug 306 is positioned, the filament 312 can be pulled thereby pulling the wire with it out of the patient.

From the foregoing, it can be seen that the pending disclosure provides an apparatus and method for closing an arteriotomy site. The apparatus and method provide for a minimally invasive procedure which has a relatively low degree of blood occlusion through the blood vessel during the application Using memory metals, a suitable backstop for the introduction of a collagen plug is easily formed and easily retracted after the collagen plug is deployed In addition, by providing collagen plugs of specific shapes, densities, and exterior configurations, the frictional interference between the collagen plug and tissue tract itself is increased thereby increasing the probability that the collagen plug will remain in place for a time duration sufficient to fully and enduringly form hemostasis at the arteriotomy site.

What is claimed is:

1. An apparatus for closing an opening in a blood vessel, comprising:
  an anchoring device having a distal end, the distal end having a linear insertion configuration and non-linear deployed configuration;
  wherein the distal end is adapted to be inserted through a tissue tract adjacent the opening in the linear insertion configuration and adapted to assume the non-linear deployed configuration after passing through the opening; and
  a biodegradable plug adapted to be inserted through the tissue tract against the anchoring device when the anchoring device is in the deployed configuration such that the distal end is disposed distally of the biodegradable plug in the non-linear configuration as the biodegradable plug is inserted;

wherein the anchoring device is removable after the biodegradable plug is deployed such that the biodegradable plug remains within the tissue tract, wherein the biodegradable plug is substantially cylindrical in shape, with a relatively rigid upper portion and a relatively malleable lower portion.

2. An apparatus for closing an opening in blood vessel comprising:

a delivery sheath having a distal end and a proximal end, the delivery sheath being insertable into a tissue tract extending from an epidermal layer to an arteriotomy site;

a length of memory metal positioned within the delivery sheath, the length of memory metal being substantially linear in shape when within the delivery sheath and being substantially non-linear in shape when extended from the delivery sheath; and a sealing plug adapted to be pushed down the tissue tract and into engagement with the length of memory metal when substantially non-linear in shape;

wherein the length of memory metal is removable after the sealing plug is deployed such that the sealing plug remains within the tissue tract, wherein the sealing plug is made of collagen, wherein the collagen plug includes a relatively hard upper portion, and a relatively soft lower portion.

* * * * *